「United States Patent」 
Hansen et al.

(10) Patent No.: US 11,304,713 B2
(45) Date of Patent: Apr. 19, 2022

(54) THROMBOSIS MACERATING AND ASPIRATION DEVICES FOR BLOOD VESSELS

(71) Applicant: Merit Medical Systems, Inc., South Jordan, UT (US)

(72) Inventors: Andrew Hansen, Bluffdale, UT (US); Alex Singleton, Sandy, UT (US); John Hall, North Salt Lake, UT (US); Christopher Cindrich, Highland, UT (US); Richard P. Jenkins, Bluffdale, UT (US); Jeremy Snow, South Jordan, UT (US); Jim Mottola, West Jordan, UT (US); Clark Ragsdale, Herriman, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 131 days.

(21) Appl. No.: 16/563,390

(22) Filed: Sep. 6, 2019

(65) Prior Publication Data

US 2020/0078029 A1 Mar. 12, 2020

Related U.S. Application Data

(60) Provisional application No. 62/793,282, filed on Jan. 16, 2019, provisional application No. 62/728,537, filed on Sep. 7, 2018.

(51) Int. Cl.
*A61B 17/221* (2006.01)
*A61B 17/3201* (2006.01)
(Continued)

(52) U.S. Cl.
CPC ........ *A61B 17/221* (2013.01); *A61B 17/3201* (2013.01); *A61B 17/320758* (2013.01);
(Continued)

(58) Field of Classification Search
CPC .............. A61B 17/221; A61B 17/3201; A61B 17/320725; A61B 17/320758;
(Continued)

(56) References Cited

U.S. PATENT DOCUMENTS

| 532,145 A | 1/1895 | Defatsch |
| 3,049,018 A | 8/1962 | Lusskin |

(Continued)

FOREIGN PATENT DOCUMENTS

| WO | 200117587 | 3/2001 |
| WO | 2018148456 | 8/2018 |

OTHER PUBLICATIONS

International Search Report and Written Opinion dated Jan. 3, 2020 for PCT/UA2019/049974.

(Continued)

*Primary Examiner* — Jocelin C Tanner
(74) *Attorney, Agent, or Firm* — Stoel Rives LLP

(57) ABSTRACT

A thrombosis macerating and aspiration device for macerating and aspirating blood clots and blockages in a blood vessel is disclosed. In some embodiments, the macerating element of the device rotates and creates a partial vacuum to assist in the aspiration of the blood clot of blockage. The macerating element may have a variety of different designs and shapes and in some embodiments, the macerating element is expandable.

5 Claims, 10 Drawing Sheets

(51) Int. Cl.
   *A61B 17/3207* (2006.01)
   *A61B 17/22* (2006.01)
   *A61B 17/00* (2006.01)
(52) U.S. Cl.
   CPC ............... *A61B 2017/00778* (2013.01); *A61B 2017/22045* (2013.01); *A61B 2017/22079* (2013.01); *A61B 2017/22084* (2013.01)
(58) Field of Classification Search
   CPC .... A61B 2017/2212; A61B 2017/2215; A61B 2017/320716; A61B 2017/22038; A61B 2017/22069; A61B 2017/22082; A61B 2017/22094; A61B 2017/00778; A61B 2017/22034; A61B 2017/22039; A61B 2017/22042; A61B 2017/22045; A61B 2017/22047; A61B 2017/22079; A61B 2017/22084; A61B 2017/320733; A61B 2017/320766
   See application file for complete search history.

(56) References Cited

U.S. PATENT DOCUMENTS

| | | | |
|---|---|---|---|
| 4,524,650 A | 6/1985 | Marks | |
| 4,527,650 A | 6/1985 | Bartholet | |
| 5,213,015 A | 5/1993 | Disston, Jr. | |
| 6,454,779 B1 | 9/2002 | Taylor | |
| 7,037,316 B2 | 5/2006 | McGuckin, Jr. et al. | |
| 7,220,269 B1* | 5/2007 | Ansel | A61B 17/22031 606/159 |
| 8,764,779 B2 | 7/2014 | Levine et al. | |
| 8,808,237 B2 | 8/2014 | Thielen et al. | |
| 8,845,621 B2 | 9/2014 | Fojtik | |
| 2001/0031981 A1 | 10/2001 | Evans et al. | |
| 2002/0029052 A1* | 3/2002 | Evans | A61M 29/02 606/159 |
| 2002/0151918 A1* | 10/2002 | Lafontaine | A61B 17/3207 606/159 |
| 2002/0169414 A1 | 11/2002 | Kletschka | |
| 2003/0040704 A1* | 2/2003 | Dorros | A61B 17/22031 604/101.04 |
| 2003/0055445 A1 | 3/2003 | Evans et al. | |
| 2005/0268750 A1 | 12/2005 | Bruce et al. | |
| 2007/0208361 A1* | 9/2007 | Okushi | A61B 17/320758 606/159 |
| 2008/0033467 A1* | 2/2008 | Miyamoto | A61B 17/320725 606/180 |
| 2008/0125798 A1* | 5/2008 | Osborne | A61B 17/221 606/159 |
| 2008/0277445 A1 | 11/2008 | Zergiebel | |
| 2009/0030274 A1 | 1/2009 | Goldfarb et al. | |
| 2010/0023033 A1* | 1/2010 | Mauch | A61B 17/22 606/159 |
| 2011/0282279 A1 | 11/2011 | Wayman et al. | |
| 2012/0059356 A1* | 3/2012 | di Palma | A61B 17/12031 604/509 |
| 2012/0239008 A1 | 9/2012 | Fojtik | |
| 2012/0277671 A1 | 11/2012 | Fuentes | |
| 2012/0316586 A1 | 12/2012 | Demarais et al. | |
| 2013/0289578 A1* | 10/2013 | Noriega | A61B 17/221 606/127 |
| 2014/0142594 A1 | 5/2014 | Fojtik | |
| 2014/0228869 A1* | 8/2014 | Bonnette | A61B 17/32037 606/159 |
| 2014/0277015 A1* | 9/2014 | Stinis | A61B 17/320725 606/159 |
| 2015/0305765 A1 | 10/2015 | Fojtik | |
| 2015/0314074 A1 | 11/2015 | Howlett et al. | |
| 2016/0015505 A1 | 1/2016 | Johnson et al. | |
| 2016/0038174 A1* | 2/2016 | Bruzzi | A61B 17/221 606/159 |
| 2016/0066933 A1* | 3/2016 | Root | A61B 17/50 606/194 |
| 2016/0270813 A1* | 9/2016 | Chida | A61B 17/22 |
| 2016/0331468 A1 | 11/2016 | Lee et al. | |
| 2017/0020556 A1* | 1/2017 | Sutton | A61B 17/320725 |
| 2017/0252057 A1 | 9/2017 | Bonnette et al. | |
| 2018/0126119 A1 | 5/2018 | McNiven et al. | |
| 2018/0242989 A1 | 8/2018 | Nita | |
| 2018/0271556 A1 | 9/2018 | Bruzzi et al. | |
| 2020/0246029 A1 | 8/2020 | Singleton et al. | |
| 2021/0077133 A1 | 3/2021 | Singleton et al. | |

OTHER PUBLICATIONS

International Search Report and Written Opinion dated Jan. 6, 2017 for PCT/US2016/053932.
Notice of Allowance dated Sep. 11, 2019 for U.S. Appl. No. 15/277,473.
Office Action dated Apr. 22, 2019 for U.S. Appl. No. 15/277,473.
Office Action dated Nov. 29, 2018 for U.S. Appl. No. 15/277,473.
SPINR Product Brochure, Rights acquired by Merit Medical Systems, Inc. ,Jul. 2015.
International Search Report and Written Opinion dated Mar. 23, 2021 for PCT/US2020/051270.
International Search Report and Written Opinion dated Jun. 1, 2020 for PCT/US2020/015721.
Office Action dated Dec. 27, 2021 for U.S. Appl. No. 16/852,105.

* cited by examiner

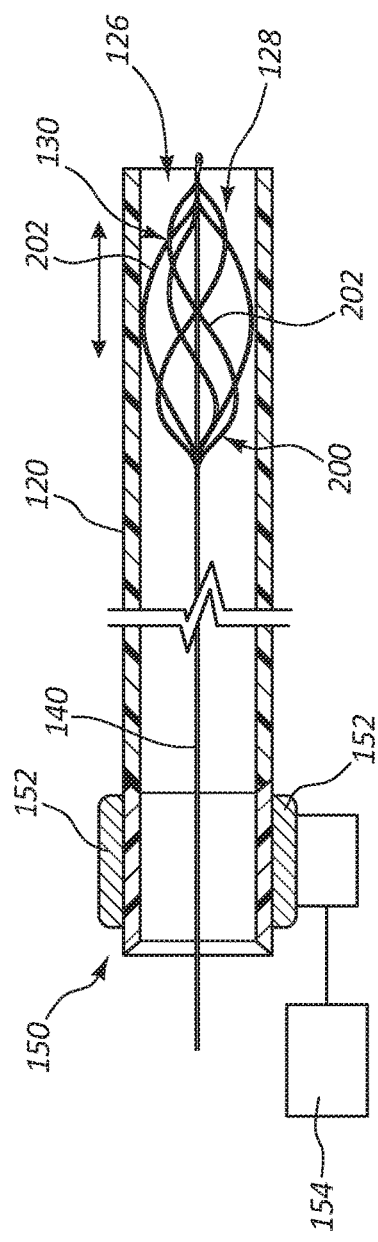
FIG. 2A
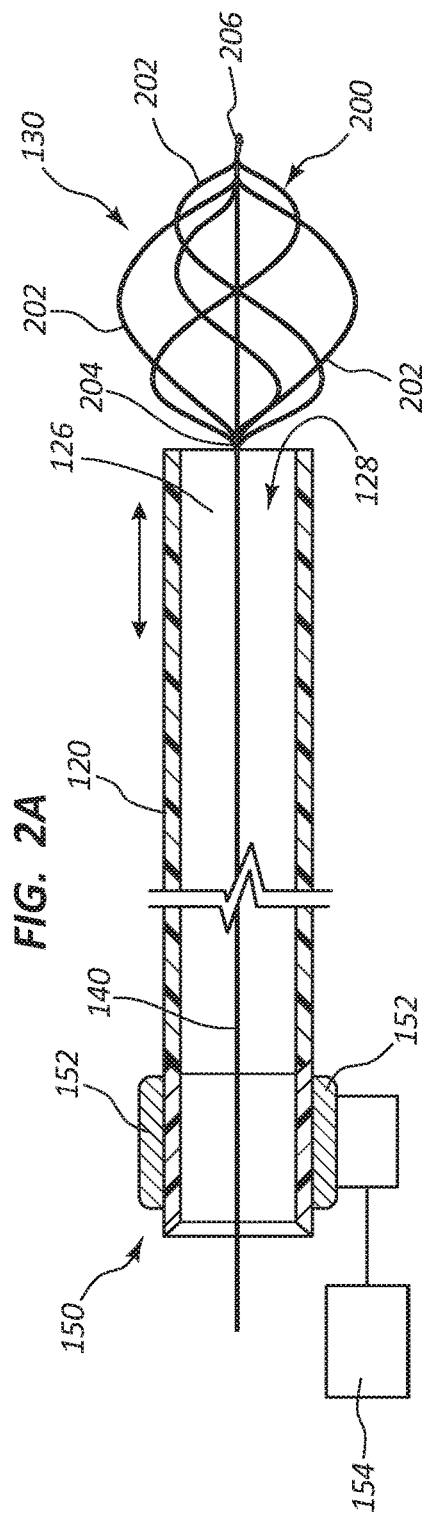
FIG. 2B
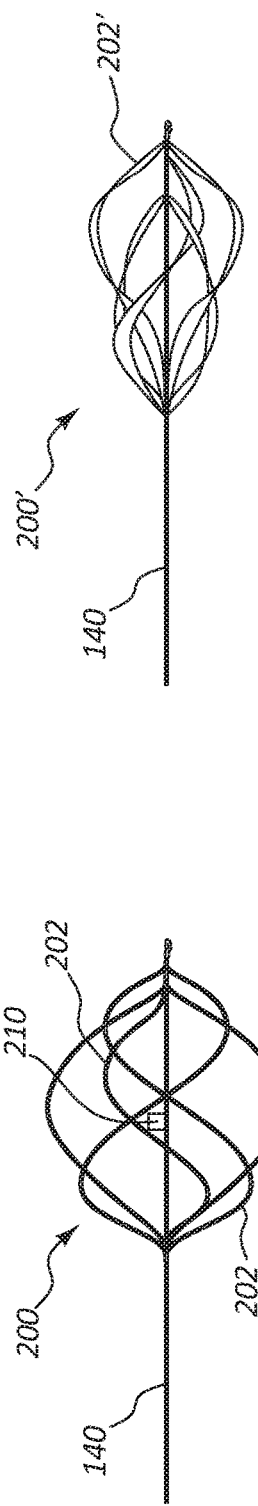
FIG. 2C
FIG. 2D

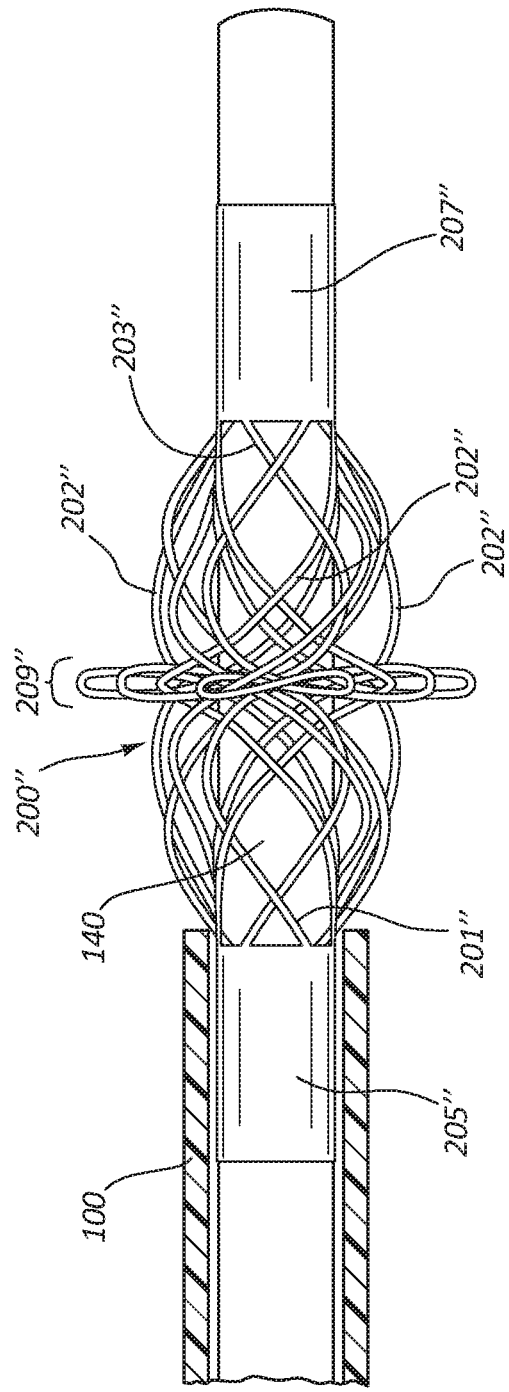
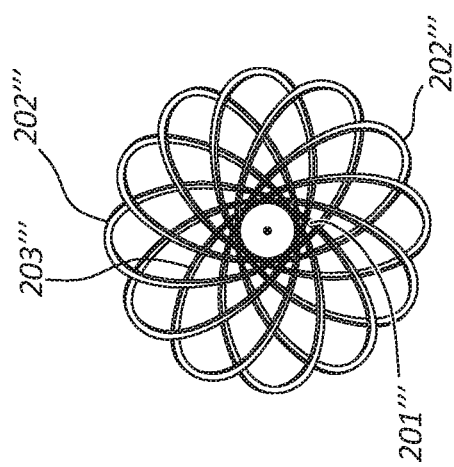
FIG. 2G
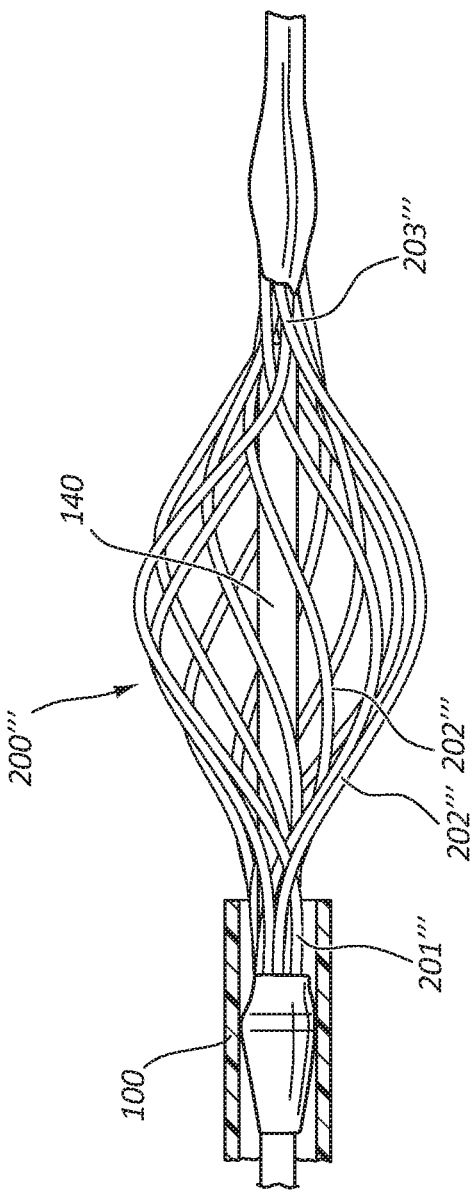
FIG. 2E
FIG. 2F

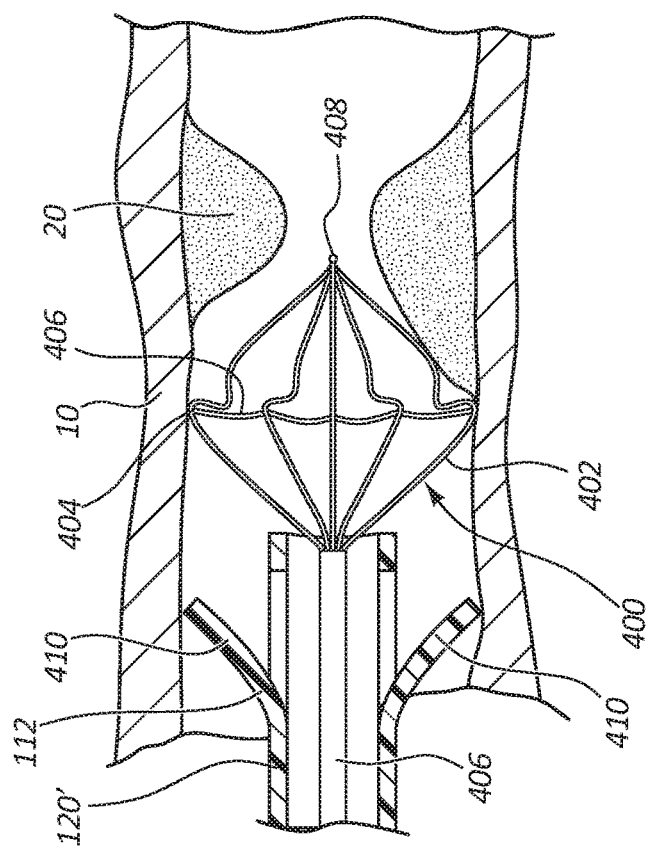
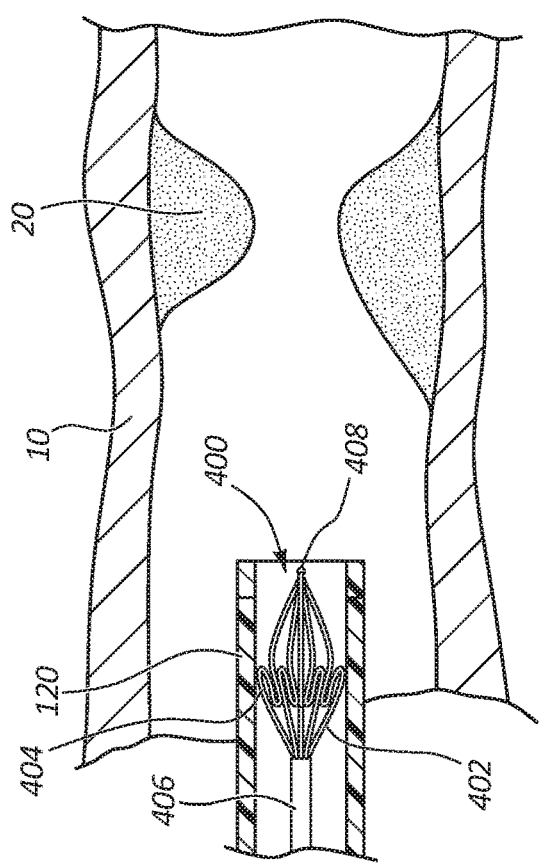
FIG. 4A
FIG. 4B

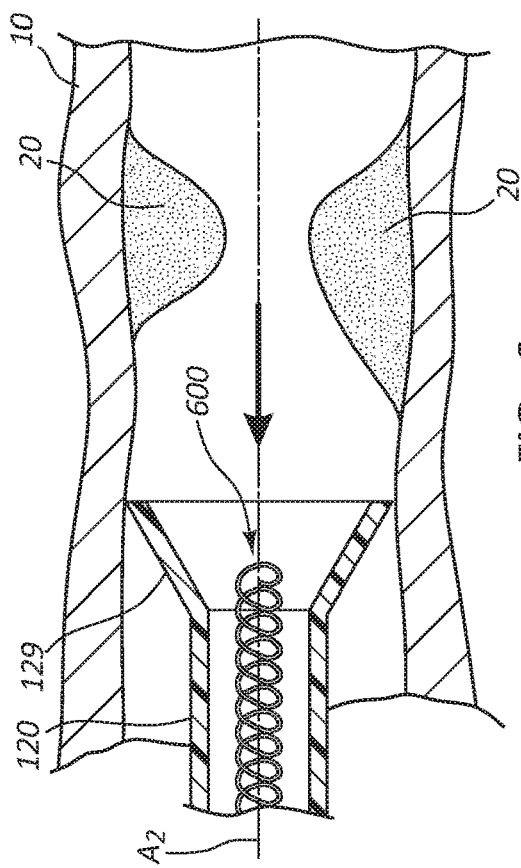
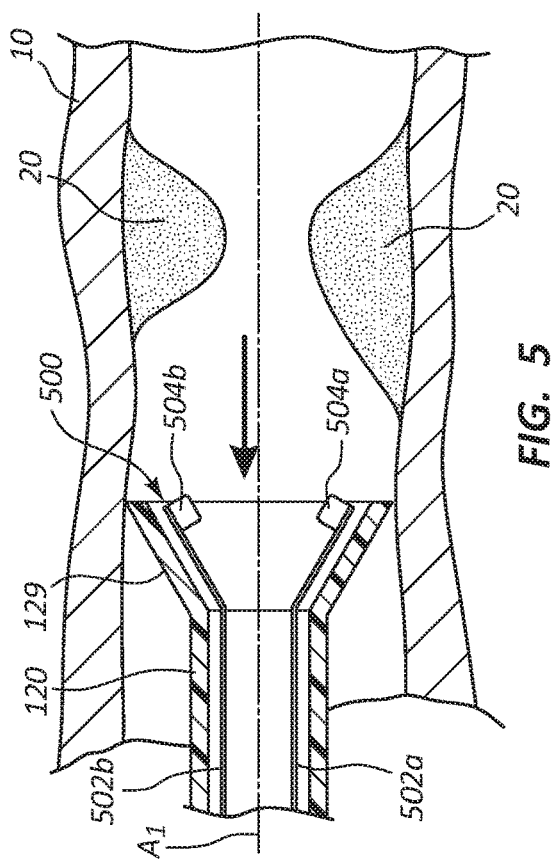

THROMBOSIS MACERATING AND ASPIRATION DEVICES FOR BLOOD VESSELS

RELATED APPLICATIONS

This application claims priority to U.S. Provisional Application No. 62/728,537, filed on Sep. 7, 2018 and titled, "THROMBOSIS MACERATING AND ASPIRATION DEVICES FOR BLOOD VESSELS" and U.S. Provisional Application No. 62/793,282 filed on Jan. 16, 2019 and titled, "THROMBOSIS MACERATING AND ASPIRATION DEVICES FOR BLOOD VESSELS," both of which are hereby incorporated by reference in their entireties.

TECHNICAL FIELD

The present disclosure relates generally to the field of medical devices. More particularly, some embodiments relates to apparatuses and methods for removing a clot from a patient's vascular system.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2A shows a catheter in a cross-sectional view and a macerating element coupled to a gear/belting system, the macerating element in a collapsed configuration according to an embodiment.

FIG. 2B shows a catheter in a cross-sectional view and a macerating element coupled to a gear/belting system, the macerating element in an expanded configuration according to an embodiment.

FIG. 2C shows a macerating element with a blade disposed within the macerating element according to an embodiment.

FIG. 2D shows a macerating element with a plurality of struts with various rates of twist.

FIG. 2E shows a macerating element with a basket shape.

FIG. 2F shows a macerating element with a basket shape.

FIG. 2G shows an end view of the macerating element of FIG. 2F.

FIG. 4A shows a catheter in a cross-sectional view and a macerating element, an s-curve stent, according to an embodiment, the s-curve stent being in a collapsed configuration.

FIG. 4B shows the s-curve stent of FIG. 4A in an expanded configuration.

FIG. 5 shows a catheter in a cross-sectional view and a macerating element, an articulating bit, according to an embodiment.

FIG. 6 shows a catheter in a cross-sectional view and a macerating element, an auger, according to an embodiment.

FIG. 7 shows a catheter in a cross-sectional view, an auger and a barbed guidewire, according to an embodiment.

FIG. 8 shows a catheter with an internal lumen and an aspiration port, according to an embodiment.

DETAILED DESCRIPTION

The field of interventional radiology, vascular surgery and cardiology may include the removal of clots in the arterial and venous systems to reduce the complications arising from vascular occlusions. Additionally, thrombosis of hemodialysis access grafts/fistulae is an issue that dialysis patients encounter wherein treatment may include clot removal. In the case of deep vein thrombosis (DVT), a disease state in which a patient has a blood clot in a peripheral vein, the clot may be removed to resolve the patient's acute symptoms or to help prevent complications of the DVT, including valve damage, Post Thrombotic Syndrome or embolization/migration of clot to the lung, a potentially fatal condition called pulmonary embolism (pulmonary artery occlusion). These clots may be removed via surgical, pharmacological, or minimally invasive mechanical or pharmacomechanical means. Techniques used for treatment of the clot include injecting/infusing a thrombolytic agent, tissue plasminogen activator (tPA), into the clot to help dissolve the clot, or alternative methods, including mechanical removal of the clot using aspiration catheters, rotational baskets, or other mechanical maceration devices.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to each other through an intermediate component.

The terms "proximal" and "distal" are opposite directional terms. For example, the distal end of a device or component is the end of the component that is furthest from the practitioner during ordinary use. The proximal end refers to the opposite end or the end nearest the practitioner during ordinary use.

Figure 1:
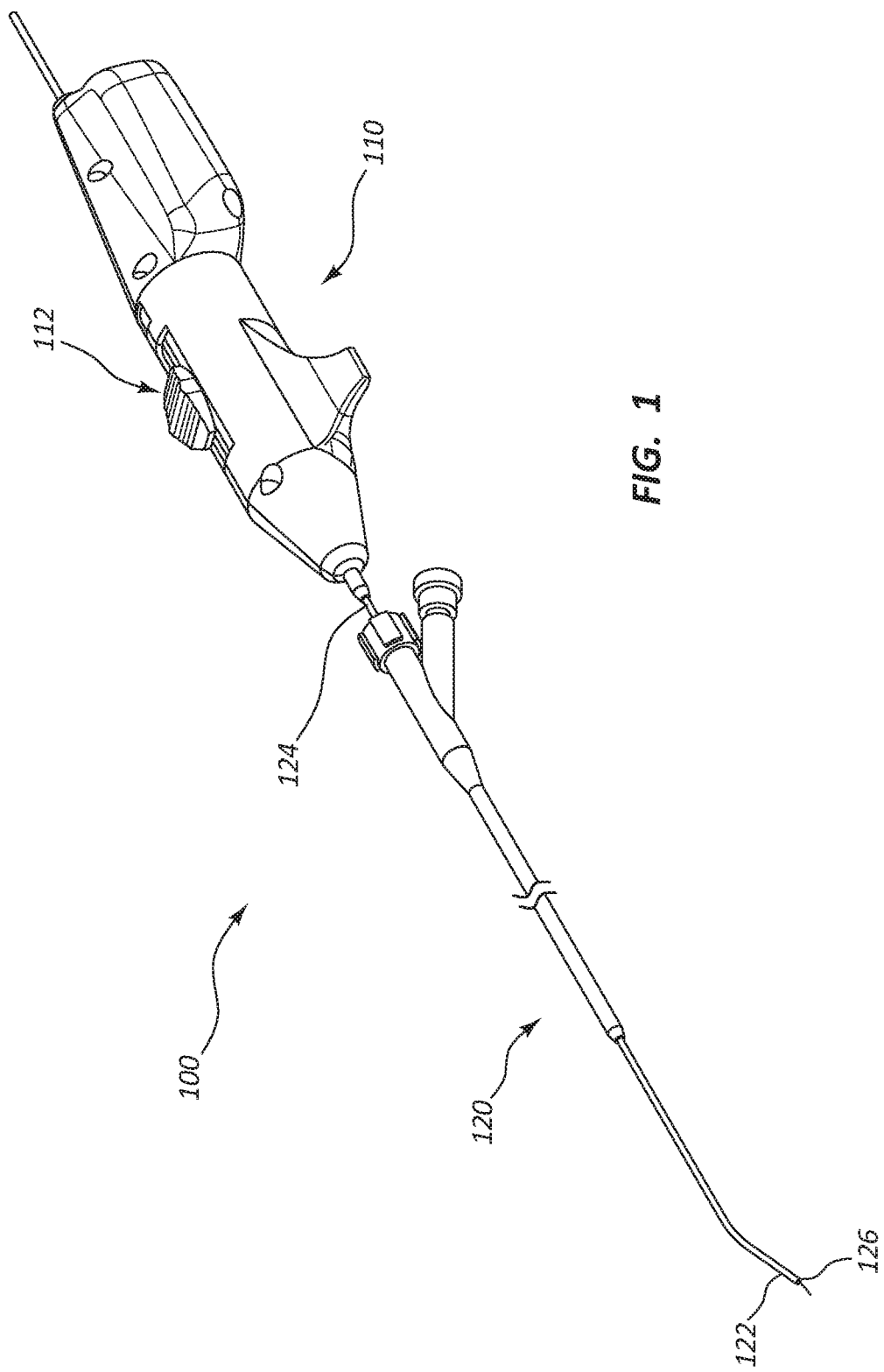
FIG. 1 shows a perspective view of a catheter and a handle, according to an embodiment.

FIG. 1 illustrates a perspective view of a catheter 100. The catheter 100 may be configured to macerate and remove a clot, such as in vascular thrombosis. The catheter 100 may include a handle 110 and a main tubular shaft 120. In some embodiments, the handle 110 includes a control portion 112, such as to control the catheter 100 while the catheter 100 is in use. The main tubular shaft 120 may be at least partially inserted within the patient's circulatory system when the catheter 100 is in use.

The main tubular shaft 120 may include a distal portion 122 and a proximal portion 124. The proximal portion 124 may be coupled to the handle 110. In the illustrated embodiments, the distal portion 122 includes an opening 126. The main tubular shaft 120 may include a plurality of tubular shafts, such as least one tubular shaft is within another tubular shaft. In some embodiments, the plurality of tubular shafts may be concentric.

The main tubular shaft 120 may further include a macerating element 130 disposed within a lumen of the main tubular shaft 120. The macerating element 130 may be configured to macerate, cut, shred, or otherwise break up a clot or other blockage in a vessel. The macerating element 130 may be disposed near the distal portion 122 of the main tubular shaft 120.

In some embodiments, the catheter 100 may include an aspiration port 128 that may be configured to aspirate the area where the macerating element 130 macerates the clot and aspirates the macerated components of the clot. In some embodiments, the aspiration port 128 is disposed along the main tubular shaft 120. The aspiration port 128 may be connected to a vacuum pump or syringe, such as to provide suction to the aspiration port 128. It will be understood by those skilled in the art, having the benefit of this disclosure, that the aspiration port 128 may be further configured to be an infusion port, such as to deliver drugs to a treatment site within the patient's vascular system.

FIGS. 2A-2B illustrate the catheter 100 in which the macerating element 130 may be connected to a guidewire 140 that extends through the lumen of the main tubular shaft 120 from the proximal portion 124 to the distal portion 122. The guidewire 140 may be configured to be rotated by a rotational member 150. The rotational member 150 may include a gearing/belt system 152 and may be rotated by a motor 154. In some embodiments, the motor 154 may be a DC motor that is integral to the handle 110. In some embodiments, the motor 154 may be an AC motor and may be powered by an AC power source.

The rotational member 150 may be disposed within the handle 110 and the speed may be controlled by controls on the handle 110. The rotational speed of the rotational member 150 may be variable and may be driven by the motor 154 and may be rotated in a clockwise or counterclockwise direction. The rotational member 150 may rotate at numerous rotational velocities, including 0-10,000 rpm. For example, the rotational member 150 may rotate at speeds of at least 500 rpm and up 10,000 rpm. In some embodiments, the rotational member 150 may rotate at speeds that range from 1,000 rpm to 5,000 rpm. In some embodiments, the rotational member 150 may rotate at speeds that range from 500 rpm to 2,500 rpm. In some embodiments, the rotational member 150 may be less than 500 rpm, and in some embodiments, less than 200 rpm.

The rotation of the rotational member 150 causes the guidewire 140 and the macerating element 130 to rotate at similar speeds and emulsify clots. In some embodiments, the rotation of the macerating element 130 may create mechanical aspiration, a partial vacuum, or otherwise accelerate particles toward the aspiration port 128. The rotation of the macerating element 130 may assist the aspiration port 128 in aspirating the components of the clot macerated by the macerating element 130.

In some embodiments, the main tubular shaft 120 is displaceable in the longitudinal direction of the main tubular shaft 120. The user may adjust the longitudinal placement of the main tubular shaft 120, which may expose the macerating element 130 outside of the main tubular shaft 120.

In some embodiments, the macerating element 130 may be expandable and may expand to increase its diameter at least two times when the macerating element 130 is displaced outside the main tubular shaft 120. In various embodiments, the macerating element 130 may expand to increase its diameter at least four times, five times, 10 times, 12 times, or 15 times.

In some embodiments, the diameter of the macerating element 130 may be controlled by the rotational speed of the macerating element 130 and/or controlled by the displacement of the main tubular shaft 120 compared to the macerating element 130. In some embodiments, the diameter of the macerating element 130 may be controlled by the user with controls in the handle 110.

FIGS. 2A and 2B illustrate a cross-sectional view of an exemplary macerating element, basket 200. FIG. 2A illustrates the basket 200 in a collapsed state and FIG. 2B illustrates the basket 200 in an expanded state. In some embodiments, the basket 200 includes two or more struts 202, such as extending from a first portion 204 of the basket 200 to a second portion 206 of the basket 200. In some embodiments, the basket 200 includes three or more struts 202, four or more struts 202, or five or more struts 202. In some embodiments, the struts 202 may be flexible, such as to conform to a portion of a patient's circulatory system or transition between the collapsed state and the expanded state.

In some embodiments, the outer or leading surface of the struts 202 may be roughened and the inner surface may be smoother than the leading surface so that the leading surface of the strut 202 encounters the clot and macerates the clot. In some embodiments, an outer surface of leading surface of the struts 202 may be smooth and the inner surface may be rougher than the leading surface. In this embodiment, the rough surface of the struts 202 emulsifies the clot and the smooth leading surface does not injure the vessel walls.

FIG. 2C illustrates another embodiment of the basket 200, which includes a propeller or blade 210 disposed within the basket 200 that rotates along with the basket 200. The blade 210 helps macerate, cut, shred, or otherwise break up the clot. The blade 210 may further create a partial vacuum directed to the aspiration port 128 to aspirate the components of the clot. In some embodiments, there may be multiple blades 210 disposed within the basket 200 that rotate along with the basket 200.

In some embodiments, the basket 200 may include multiple struts 202. In some embodiments, the struts 202 may have the same height. In some embodiments, the struts 202 may have differing heights. In some embodiments, the struts 202 may have different lengths, giving the struts 202 differing heights. In some embodiments, a peak (max height) of each strut 202 may be disposed in different locations over the length of the struts 202. In some embodiments, the peak of some of the struts may be centrally disposed, the peak of other struts may be disposed near a distal end of the basket 200, and the peak of other struts may be disposed near a proximal end of the basket 200. In some embodiments, the struts 202 may be fabricated from a material that provides sufficient stiffness to macerate and emulsify the clots but flexible enough to ride over and not damage the venous or arterial structures, such as valves. In some embodiments, the struts 202 may be made from a memory material, such as Nitinol, so that the basket 200 achieves a predetermined shape when the basket 200 is expanded.

FIG. 2D illustrates an embodiment of a basket 200' in which each strut 202' has a spiral or rate of twist. The rate of twist extends over the length of each strut 202'. In some embodiments, the rate of twist is a single twist over the length of the strut 202'. In some embodiments, the rate of twist is two twists over the length of the strut 202'. In some embodiments, the rate of twist is greater than two twists over the length of the strut 202'. The rate of twist of each strut 202' may help create a partial vacuum directed toward the aspiration port 128 when the basket 200' is expandable and rotated. In some embodiments, the rate of twist for each strut 202' is the same over the length of each strut 202'. In some embodiments, multiple struts 202' may have the same rate of twist over the length of the strut 202' and other struts 202' may have different rates of twist.

FIG. 2E illustrates an embodiment of a basket 200" with a plurality of struts 202". The struts 202" each have a first end 201" and a second end 203". The first end 201" may be fixed to a first basket end 205" and the second end 203" may be fixed to a second basket end 207". The first basket end 205" and the second basket end 207" may move relative to each other. For example, when the first basket end 205" moves toward the second basket end 207", the basket 200" may expand, increasing the diameter of the basket 200". When the first basket end 205" moves away from the second basket end 207", the basket 200' may collapse, decreasing the diameter of the basket 200" and enabling the basket 200" to fit within the catheter 100. In some embodiments the basket 200" may have a central portion 209" that has a greater diameter than the rest of the basket 200". Each strut 202" may spiral around the guidewire 140. In some embodiments, the first end 205" is attached to the guidewire 140 and the second end 207" may be able to move relative to the guidewire 140 to enable the expansion and collapse of the basket 200". In other embodiments, the second end 207" may be attached to the guidewire 140 and the first end 205" may be able to move relative to the guidewire 140.

In some embodiments, the struts of the different embodiments of the basket may be flat wire, a round wire, or some struts may be flat wire and other struts may be round wire.

FIGS. 2F-2G illustrate an embodiment of a basket 200''' with a plurality of struts 202'''. The struts 202''' may be cut from a metal tubing in a predetermined pattern. The struts 202''' may be cut in a vareity of different manners, for example, laser cutting, mechanical cutting, plasma cutting, flame cutting, waterjet cutting, etc. Each strut 202''' may have a first end 201''' and a second end 203'''. Each strut 202''' may spiral around the guidewire 140 in the range of 360 degrees to 540 degrees. FIG. 2G illustrates an end view of the basket 200''' illustrating the range of rotation of the struts 202''' from the first end 201''' to the second end 203'''.

Figure 3B:
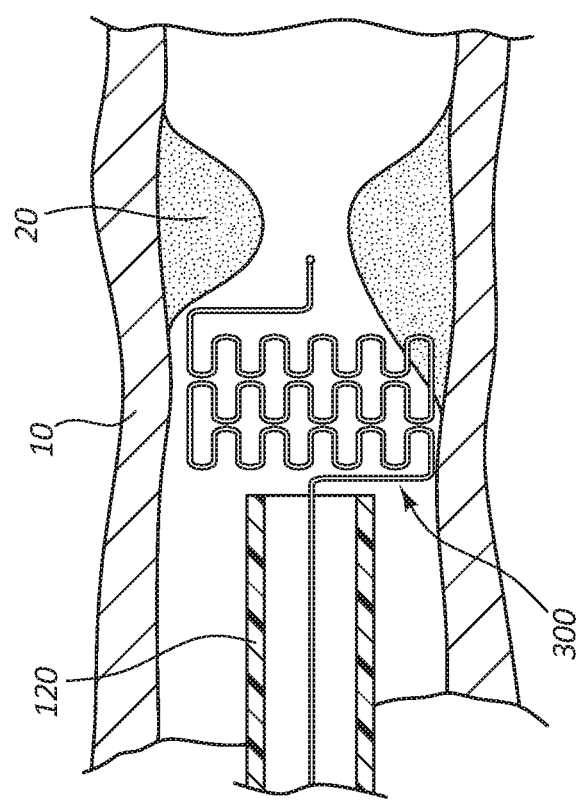
FIG. 3B shows the wire wound stent of FIG. 3A in an expanded configuration.
Figure 3A:
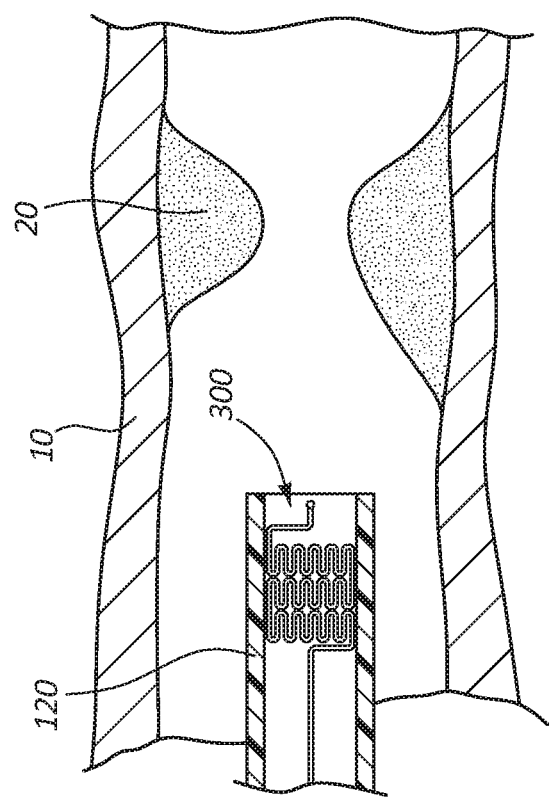
FIG. 3A shows a catheter in a cross-sectional view and a macerating element, a wire wound stent, according to an embodiment; the wire wound stent being in a collapsed configuration.

FIGS. 3A and 3B illustrate a cross-sectional view of another exemplary embodiment of a macerating element, a wire wound stent 300. FIG. 3A illustrates the main tubular shaft 120 disposed within a vessel 10 and the wire wound stent 300 in a collapsed state within the main tubular shaft 120. FIG. 3B illustrates the stent in an expanded state outside the main tubular shaft 120. The wire wound stent 300 may expand to a round cylindrical shape. The wire wound stent 300 expands when the main tubular shaft 120 is displaced relative to the longitudinal direction of the main tubular shaft 120 and exposes the wire wound stent 300. When the wire wound stent 300 is outside the main tubular shaft 120, the wire wound stent 300 may be rotated to macerate the clot or blockage 20. Rotation of the wire wound stent 300 may create mechanical aspiration, a partial vacuum, or otherwise accelerate clots toward the aspiration port 128 to aspirate the components of the macerated clot.

The structure of the wire wound stent 300 may include a plurality of u-shaped turns disposed throughout the wire wound stent 300. In the illustrated embodiments, the wire wound stent 300 includes a plurality of rows, each row with a plurality of u-turns. In a collapsed and unexpanded state, the u-shaped turns are crimped, thus allowing the wire wound stent 300 to fit within the lumen of the main tubular shaft 120. When the wire wound stent 300 is disposed outside the main tubular shaft 120, the u-shaped turns expand, thus expanding the entire wire wound stent 300. The wire wound stent 300 is configured to expand to a predetermined size.

FIGS. 4A and 4B illustrate a cross-sectional view of another exemplary embodiment of a macerating element, an s-curve stent 400. FIG. 4A illustrates the s-curve stent 400 in a collapsed state, and FIG. 4B illustrate the s-curve stent 400 in an expanded state outside the main tubular shaft 120'. The s-curve stent 400 in the expanded state may have a round cylindrical shape. In the illustrated embodiment, the main tubular shaft 120' includes barbs 410 that may engage with the vessel 10 to secure the main tubular shaft 120' in place while the s-curve stent 400 is rotated. The s-curve stent 400 expands when the main tubular shaft 120' is displaced relative to the longitudinal direction of the main tubular shaft 120' and exposes the s-curve stent 400. When the s-curve stent 400 is outside the main tubular shaft 120', the s-curve stent 400 may be rotated to macerate the clot or blockage. Rotation of the s-curve stent 400 may create mechanical aspiration, a partial vacuum, or otherwise accelerate clots toward the aspiration port 128 to aspirate the components of the macerated clot.

The structure of the s-curve stent 400 includes a plurality of struts 402 that each include an s-curve 404. The s-curves 404 of each strut 402 are laterally connected to adjacent s-curves 404 by a connector 406. The distal ends of each s-curve 404 are coupled together at a distal end 408. The proximal ends of each s-curve 404 are coupled to a sheath 406 that is disposed over guidewire 140. When a pulling force is applied by the user to the sheath 406, the s-curves 404 are extended, which creates a radial expansion. The radial expansion of the s-curve stent 400 changes the structure of the s-curves 404, creating a stretch s-curve, with the connectors 406 and the middle portion of the s-curve 404 being substantially linear.

FIG. 5 illustrates a cross-sectional view of another exemplary embodiment of a macerating element, an articulating bit 500 disposed within the main tubular shaft 120 near the distal end. In the illustrated embodiment, the articulating bit 500 includes multiple bits 504a, 504b that are attached to separate guidewires 502a, 502b. The guidewires 502a, 502b and bits 504a, 504b may rotate about an axis of rotation A1. The articulating bit 500 may be rotated to macerate the clot or blockage. Rotation of the articulating bit 500 may further produce mechanical aspiration, a partial vacuum, or otherwise accelerate components of the clot or blockage to the aspiration port 128. In some embodiments, the main tubular shaft 120 may include a scoop 129. The scoop 129 may extend radially away from the axis of rotation A1 at a predetermined angle. The scoop 129 may interface with the walls of the vessel to help prevent the articulating bit 500 from coming in contact with the vessel walls. In some embodiments, the scoop 129 may help keep clots from passing. FIG. 5 illustrates two bits 504*a*, 504*b*, but articulating bit 500 may include more or fewer than two bits 504*a*, 504*b*.

FIG. 6 illustrates a cross-sectional view of another exemplary embodiment of a macerating element, an auger 600. The auger 600 may have a helical bit for macerating the clot or blockage. The auger 600 may rotate about an axis of rotation A2. The auger 600 may extend from the proximal portion 124 to the distal portion 122 of the main tubular shaft 120, but not extend beyond the distal portion 122 of the main tubular shaft 120. In some embodiments, the main tubular shaft 120 includes the scoop 129.

FIG. 7 illustrates a cross-sectional view of a macerating element, an auger 700, and a barbed guidewire 710. The barbed guidewire 700 may include a plurality of barbs that extend in a proximal direction at a predetermined angle from the barbed guidewire 700. The displacement of the barbed guidewire 700 may be controlled by the user, enabling the user to extend the barbed guidewire 700 beyond the distal portion 122 of the main tubular shaft 120. The user may extend the barbed guidewire 700 to interact with the clot or blockage and direct the clot or blockage toward auger 600 and pull the clot or blockage toward the auger 600.

FIG. 8 illustrates an alternative embodiment of the main tubular shaft 120'. The main tubular shaft 120' may include an additional internal lumen 121' that is disposed within the main tubular shaft 120'. The internal lumen 121' has a diameter less than the diameter of the main tubular shaft 120'. In some embodiments, the diameter of the internal lumen 121' is half the diameter of the main tubular shaft 120'. In some embodiments, the diameter of the internal lumen 121' is a fourth of the diameter of the main tubular shaft 120'. The internal lumen 121' may be coupled to the main tubular shaft 120' by a plurality of connectors 119' that extend from the internal lumen 121' to the main tubular shaft 120'. The internal lumen 121' may house the macerating element. In some embodiments, the macerating element may be extended beyond the distal end of the internal lumen 121' to allow the macerating element to macerate the clot. As discussed previously, the macerating element may be expandable.

In addition, the main tubular shaft 120' may further include an aspiration port 128'. The aspiration port 128' aspirates the components of the clot or blockage as the macerating element macerates the clot or blockage. The aspiration port 128' may coincide with the main tubular shaft 120'.

Figure 9A:
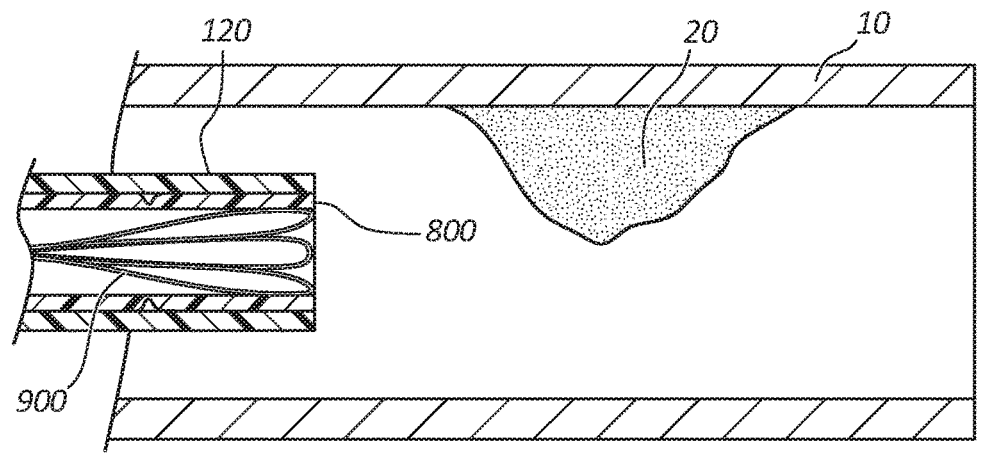
FIG. 9A shows a catheter and an internal lumen in a cross-sectional view and a macerating element, according to an embodiment.
Figure 9B:
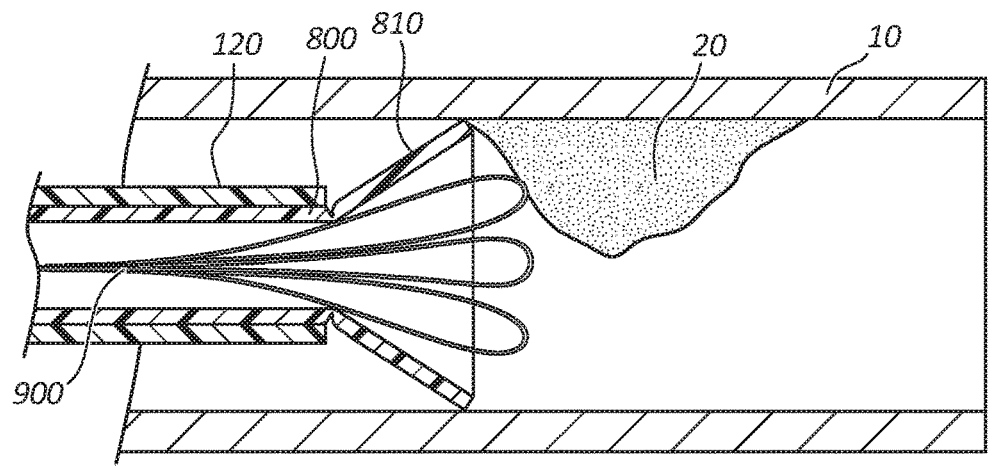
FIG. 9B shows the catheter of FIG. 9A with a deployed internal lumen forming a scoop, according to an embodiment.
Figure 9C:
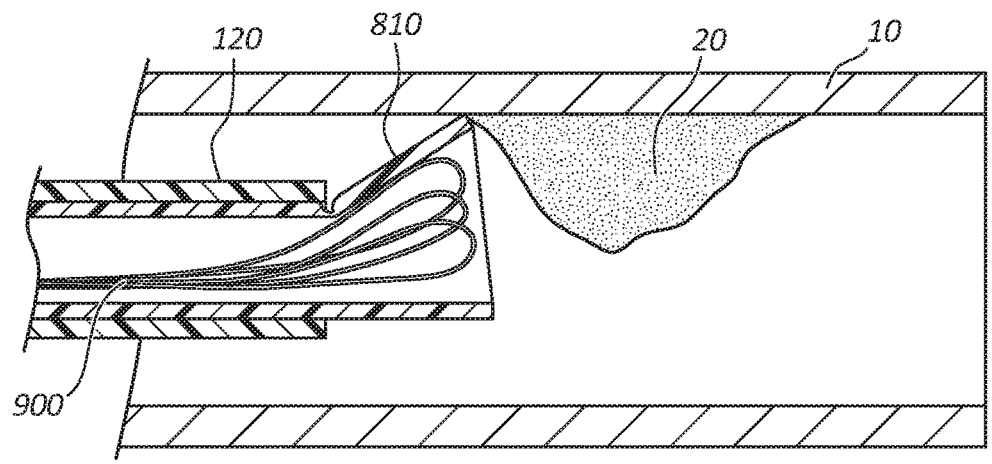
FIG. 9C shows the catheter and deployed internal lumen of FIG. 9B, with the lumen directed in a new direction, according to an embodiment.

FIGS. 9A-9C illustrate a cross-sectional view of the main tubular shaft 120 with the macerating element 900, such as a plurality of snare loops (discussed later in relation to FIGS. 10A-10C), and an additional internal lumen 800. The diameter of the internal lumen 800 may be slightly smaller than the diameter of the main tubular shaft 120, and the internal lumen 800 is configured to slide relative to the main tubular shaft 120. FIG. 9A illustrates the internal lumen 800 disposed completely within the main tubular shaft 120.

FIG. 9B illustrates a cross-sectional view of the main tubular shaft 120 and the internal lumen 800 after the internal lumen 800 has been deployed. When the internal lumen 800 extends beyond the distal portion 122 of the main tubular shaft 120, a scoop 810 extends away from the main tubular shaft 120 at a predetermined angle. The scoop 810 may interact with the vessel wall and help prevent the auger 600 from damaging the vessel wall. The scoop 810 may be similar to scoop 129 previously described.

In some embodiments, the scoop 810 may be steerable by a user. For example, the user may be able to provide a pulling force to a portion of the internal lumen 800 to direct the direction of the scoop 810. For example, if a pulling force is applied to a top portion of the internal lumen 800 as illustrated in FIG. 9C, the scoop 810 is directed to the top of the vessel. In this manner, the user may direct the scoop 810 toward the clot or blockage.

Figure 10A:
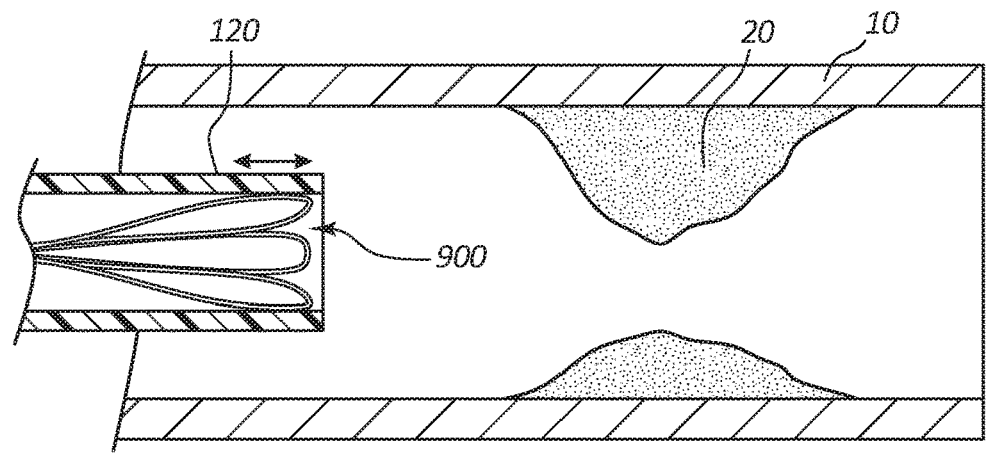
FIG. 10A shows a catheter in a cross-sectional view and a macerating element in a undeployed configuration, according to an embodiment.
Figure 10B:
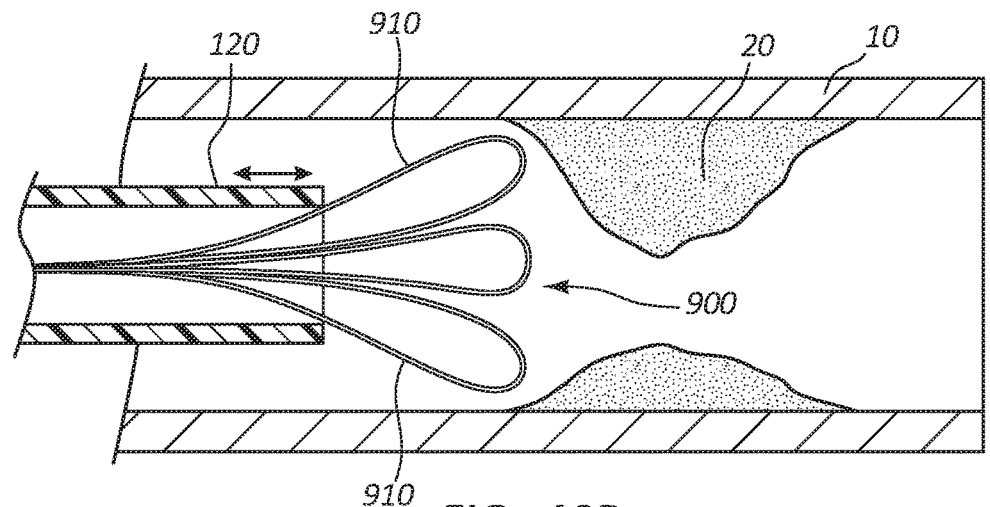
FIG. 10B shows the catheter and the macerating element of FIG. 10A in a deployed configuration.

FIG. 10A illustrates a cross-sectional view of another exemplary embodiment of a macerating element, a snare loop macerating element 900. The snare loop macerating element 900 may include a plurality of snare loops 910 that extend the length of the main tubular shaft 120. Each snare loop 910 has a loop that is formed near the distal end of the snare loop 910. In some embodiments, the snare loops 910 may be rotated within the main tubular shaft 120 to macerate the clot or blockage. In some embodiments, the main tubular shaft 120 may be displaced to deploy the snare loops 910 outside of the main tubular shaft 120, as illustrated in FIG. 10B. In some embodiments, the snare loops 910 may be extended beyond the distal portion 122 of the main tubular shaft 120.

The user may control the macerating diameter of the snare loop macerating element 900. The macerating diameter refers to the diameter of a circumferential path that the distal ends of the snare loops 910 travel while being rotated. The rotation of the snare loops 910 and the distance that the snare loops 910 are outside the main tubular shaft 120 determine the macerating diameter. For example, the greater the speed of rotation, the greater the macerating diameter of the snare loop macerating element 900. Also, the greater the distance the snare loop macerating element 900 is outside the main tubular shaft 120, the greater the macerating diameter.

Figure 10C:
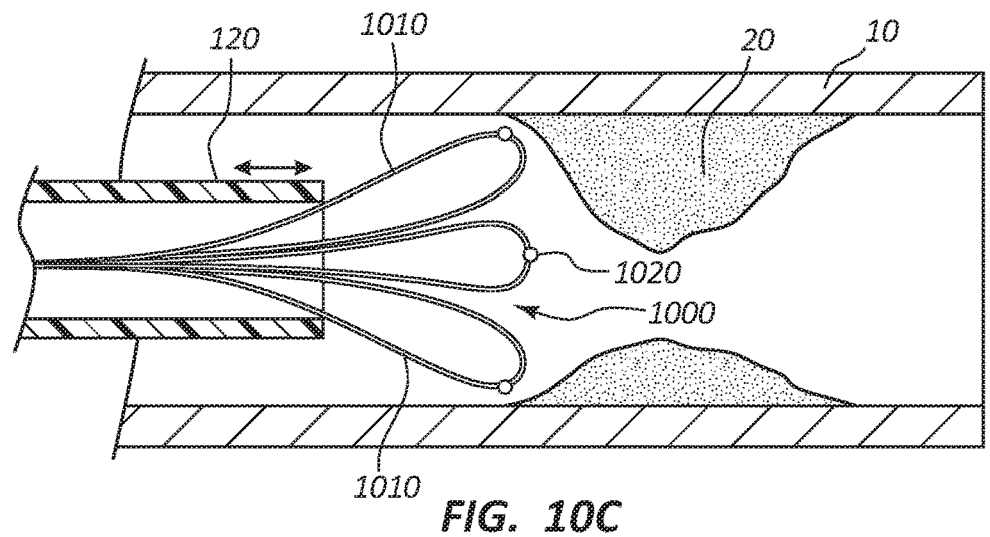
FIG. 10C shows a catheter and a macerating element with weighted ends, according to an embodiment.

FIG. 10C illustrates an embodiment of a snare loop macerating element 1000. Snare loops 1010 may include additional weight 1020 at the tips of the snare loops 1010. In some embodiments, the wire of the snare loops 1010 may have a tapered diameter at the tips of the snare loops 1010 to add additional weight at the tips. In some embodiments, the tips include a coating that adds additional weight to the tips of the snare loops 1010. The coating may be a low-friction, smooth coating so that the tips of the snare loops 1010 are atraumatic to the vessel walls.

Figure 11A:
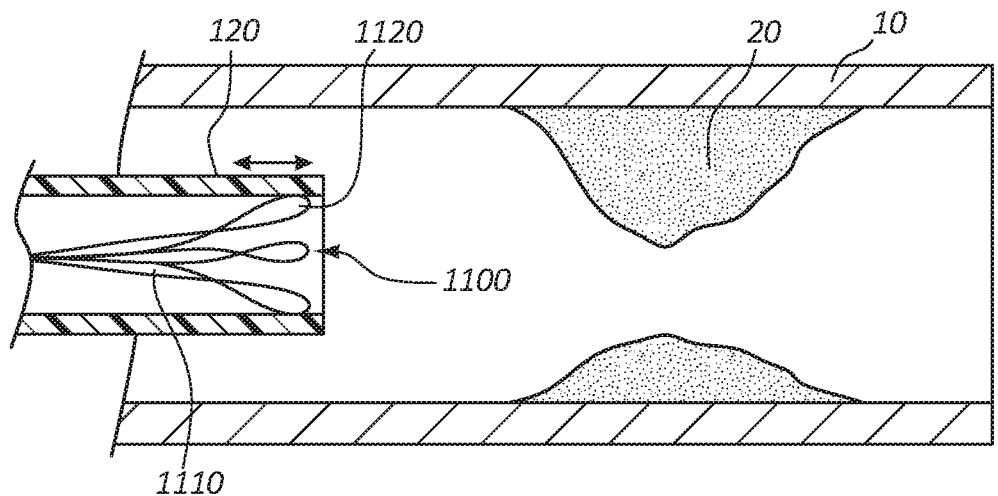
FIG. 11A shows a catheter in a cross-sectional view and a macerating element in an undeployed configuration, according to an embodiment.
Figure 11B:
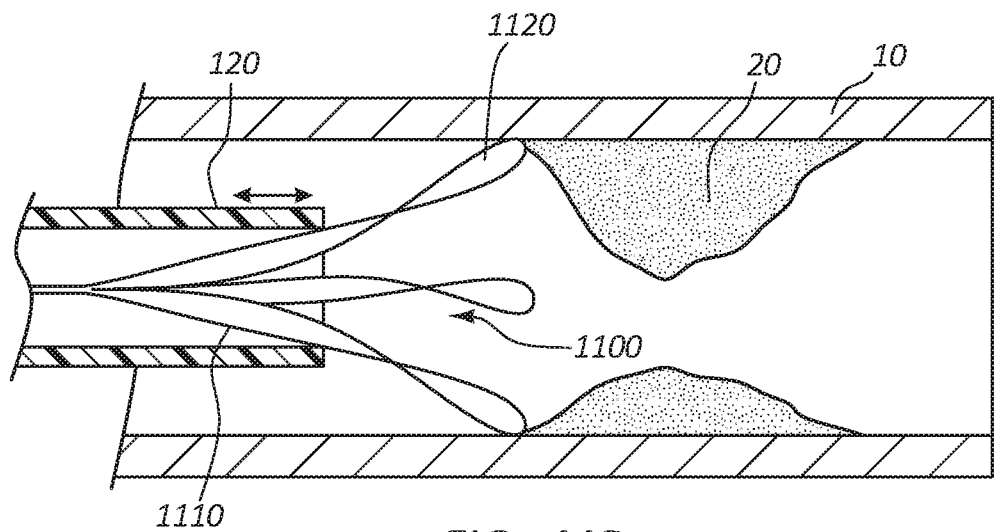
FIG. 11B shows the catheter and the macerating element of FIG. 11A in a deployed configuration.

FIGS. 11A and 11B illustrate an embodiment of a dual loop macerating element 1100. FIG. 11A illustrates the dual loop macerating element 1100 in a collapsed configuration and FIG. 11B illustrates the dual loop macerating element 1100 in an expanded configuration. Similar to the snare loop macerating element 900, the dual loop macerating element 1100 may include a plurality of dual loop wires 1110. In some embodiments, the dual loop wires 1110 includes two loops near the distal end of the dual loop wire 1110.

Similar to the snare loop macerating element 900, the user may control the macerating diameter of the dual loop macerating element 1100. The rotation of the dual loop wires 1110 and the distance that the dual loop wires 1110 are outside the main tubular shaft 120 determine the macerating diameter. For example, the greater the speed of rotation, the greater the macerating diameter of the dual loop macerating element 1100. Also, the greater the distance the dual loop macerating element 1100 is outside the main tubular shaft 120, the greater the macerating diameter.

Figure 12A:
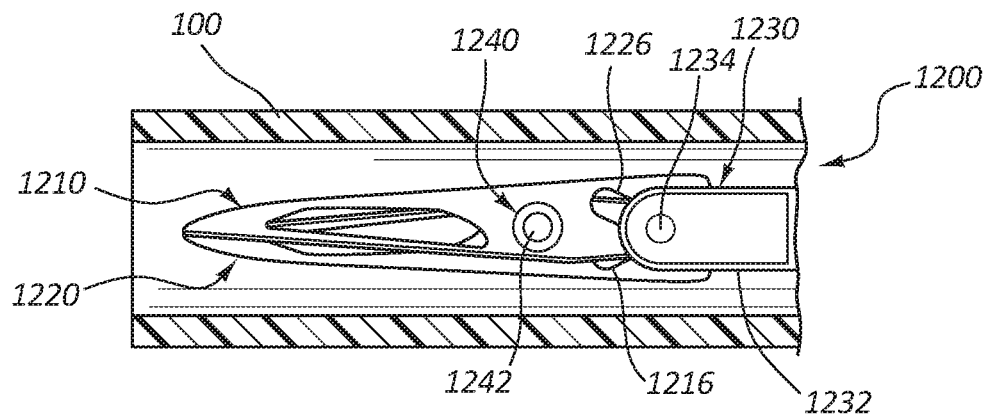
FIG. 12A show a catheter and a macerating element with a scissor-shape configuration in a collapsed state.
Figure 12B:
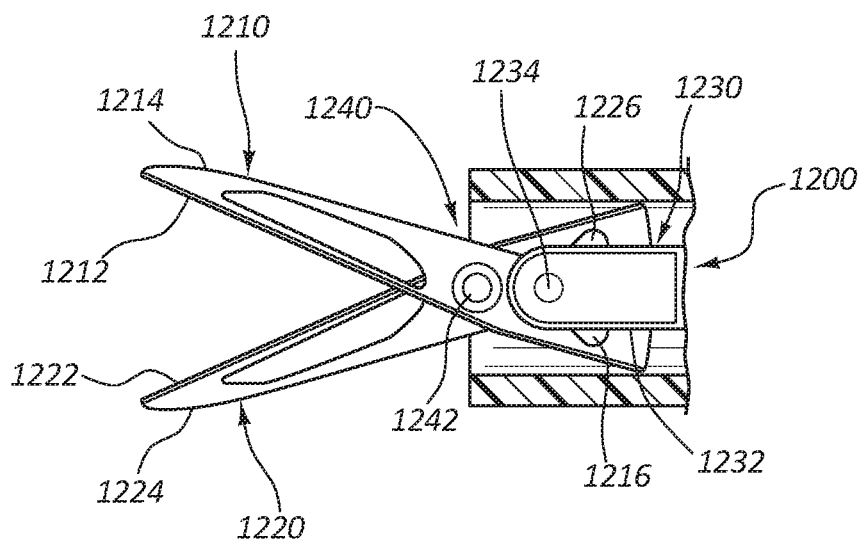
FIG. 12B shows the catheter and the macerating element of FIG. 12A in an expanded configuration.
Figure 12C:
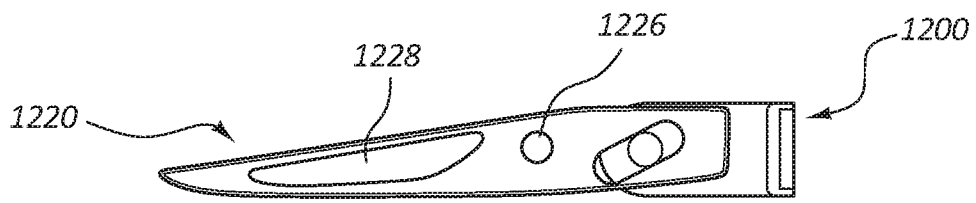
FIG. 12C shows a bottom blade of the macerating element of FIG. 12A.

FIGS. 12A-12C illustrate an embodiment of a dual blade macerating element 1200. The dual blade macerating element 1200 illustrated in FIGS. 12A-12B have two blades, a top blade 1210 and a bottom blade 1220, forming a scissor-like shape. However, the macerating element 1200 may include more than two blades. FIG. 12 illustrates the dual blade macerating element 1200 in a collapsed configuration and disposed within the catheter 100. FIG. 12B illustrates the dual blade macerating element 1200 in an expanded configuration after macerating element 1200 has been advanced out of the catheter 100. This may be accomplished by having the catheter 100 slide back or by having the macerating element 1200 advance out of the catheter 100.

The expansion of the macerating element 1200 may be accomplished in a number of different ways. For example, the macerating element 1200 may include a pull hinge system 1230. The pull hinge system 1230 may include a housing 1232, a pin or hinge 1234 that extends through the housing 1230 and through apertures 1216 and 1226 of each blade 1210 and 1220. The apertures 1216 and 1226 may have an oval shape and the hinge 1234 is slidable along the length of the apertures 1216 and 1226.

A user may control the expansion of the macerating element 1200 may applying a distal or proximal oriented force to the housing 1232 of the pull hinge system 1230. When a distal oriented force is applied to the housing 1232, the hinge 1234 advances along the length of the apertures 1216 and 1226, which causes the blades 1210 and 1220 to rotate about an axis of rotation 1240 and away from each, expanding the macerating element 1200.

The axis of rotation may be a pin the extend through both blades 1210 and 1220 of the macerating element 1200. FIG. 12C illustrates the bottom blade 1220 which includes an aperture 1226 in the bottom blade 1220 for the pin 1242 to extend through, thus creating the axis of rotation for the bottom blade 1220. The top blade 1210 includes a similar aperture for the pin 1242 to extend through.

A user may collapse the macerating element 1200 by applying a proximally oriented force to the housing 1232, which pulls the hinge 1234 along the length of the apertures 1216 and 1226 and the blades 1210 and 1220 rotate about axis of rotation 1240 and toward each other and close the macerating element 1200.

When the macerating element 1200 is expanded, the macerating element 1200 may be rotated to emulsify clots in the vessel. For example, each blade 1210 and 1220 of the macerating element 1200 may include an edge 1212, 1222 that helps macerate, cut, shred, or otherwise break up the clot. The edges 1212, 1222 may be sharpened to macerate the clot or the edges 1212, 1222 may be roughened to macerate the clot. The rotation of the blades 1210 and 1220 may further create a partial vacuum directed to an aspiration port to aspirate the components of the clot.

Each blade 1210 and 1220 may further include an outer edge 1214 and 1224. The outer edges 1214 and 1224 may be smooth or include a low-friction, smooth coating so that the outer edges 1214 and 1224 are atraumatic to the vessel wall while the macerating element 1200 is rotating.

Each blade 1210 and 1220 may further include an additional aperture, such as the aperture 1228 shown in FIG. 12C. The aperture 1228 may lighten the weight of the blade 1210.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A catheter for macerating a blockage or clot, comprising:
   a main tubular shaft having a distal end and a proximal end;
   a guidewire disposed in the main tubular shaft;
   a macerating element disposed on the guidewire adjacent the distal end, the macerating element comprising a plurality of struts that are expandable when the macerating element is disposed out of the main tubular shaft; and
   a blade disposed within the macerating element on the guidewire, the blade configured to mechanically aspirate while it rotates.

2. The catheter of claim 1, wherein at least one of the plurality of struts has a rate of twist that extends from a first end of the strut to a second end of the strut.

3. The catheter of claim 2, wherein each strut has a different rate of twist.

4. The catheter of claim 1, wherein each strut rotates about the guidewire, each strut rotating between 360 degrees to 540 degrees of rotation around the guidewire from a first end of each strut to a second end of the strut.

5. The catheter of claim 1, wherein a first end of each strut is fixed to a first basket end and a second end of each strut is fixed to a second basket end, wherein the first basket end is configured to axially move relative to the second basket end, wherein axial movement of the first basket end toward the second basket end expands the basket, and wherein axial movement of the first basket end away from the second basket end collapses the basket.

\* \* \* \* \*